United States Patent [19]

Plante et al.

[11] Patent Number: 4,495,587
[45] Date of Patent: Jan. 22, 1985

[54] AUTOMATIC NONDESTRUCTIVE ROLL DEFECT INSPECTION SYSTEM

[75] Inventors: Arcade J. Plante, Center Valley; Richard F. Wetzel, Bath, both of Pa.

[73] Assignee: Bethlehem Steel Corporation, Bethlehem, Pa.

[21] Appl. No.: 328,345

[22] Filed: Dec. 8, 1981

[51] Int. Cl.³ ............... G01N 27/82; G01N 29/04
[52] U.S. Cl. ................................ 364/507; 73/602; 324/208; 324/226; 324/237; 364/552
[58] Field of Search ............ 364/469, 472, 507, 550, 364/551, 552; 324/237, 238, 240, 208, 226; 73/607, 618, 634, 637, 602

[56] References Cited

U.S. PATENT DOCUMENTS

| | | | |
|---|---|---|---|
| 2,519,367 | 8/1950 | Gunn et al. | 324/240 |
| 3,939,404 | 2/1976 | Tait | 324/238 |
| 4,064,452 | 12/1977 | Toth | 324/238 |
| 4,191,922 | 3/1980 | Harris et al. | 324/238 |
| 4,207,520 | 6/1980 | Flora et al. | 324/238 |
| 4,209,744 | 6/1980 | Gerasimov | 324/241 |
| 4,213,183 | 7/1980 | Barron et al. | 364/552 |
| 4,247,819 | 1/1981 | Shimada et al. | 324/237 |
| 4,303,885 | 12/1981 | Davis et al. | 324/237 |
| 4,353,257 | 10/1982 | Vrba et al. | 364/507 |

OTHER PUBLICATIONS

P. Keller, "A New Technique for Noncontact Temperature Measurements of Rotating Rolls," *Iron and Steel Engineer*, May, 1980, pp. 42–44.

*Primary Examiner*—Errol A. Krass
*Assistant Examiner*—Edward R. Cosimano
*Attorney, Agent, or Firm*—John J. Selko

[57] ABSTRACT

A computer-based eddy current nondestructive or ultrasonic testing system automatically inspects rolling mill roll surface defects during roll grinding operations comprising articulated probe means, eddy current, or ultrasonic, test instrument means, computer means, display and printer means. The articulated probe mechanism is mounted on a traversing roll grinder carriage, is automatically positioned over the test roll in response to control means initiated by the grinder operator, and has a probe head with a controlled fluid bearing, air or liquid, to automatically maintain probe-head-to-test roll gap. One or multiple eddy current, or ultrasonic, probes in the test head generate anamoly test signals, which, together with a probe head temperature sensor signal, are processed in a modified test instrument and the computer. Computer plots defects signals as color bars vs. probe position and displays these bars graphically and other messages on a color CRT display and/or a graph printer. This system arrangement provides for effective roll surface defect inspection by grinder personnel, and others, who ordinarily are unskilled in NDT test and analysis methods.

6 Claims, 17 Drawing Figures

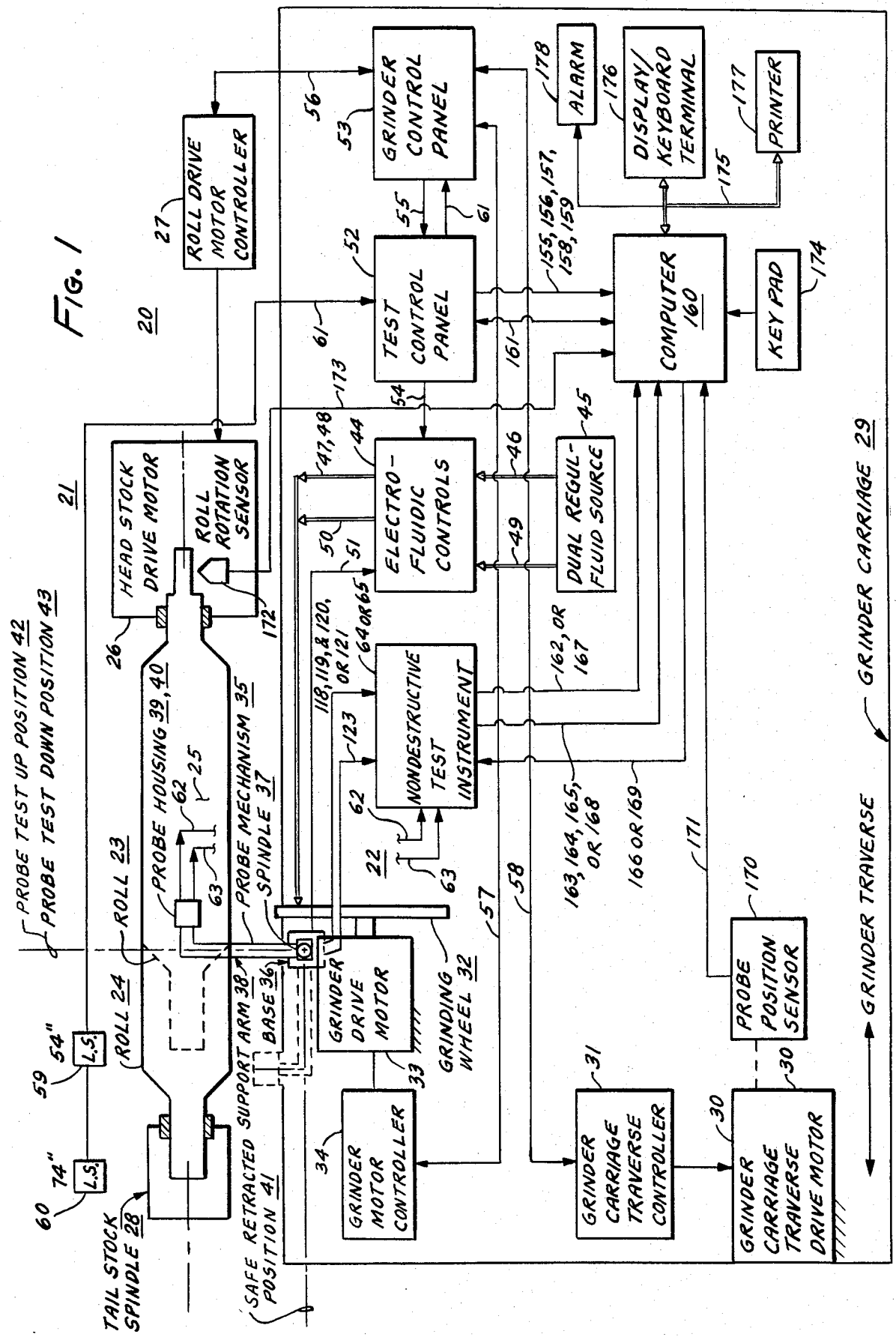

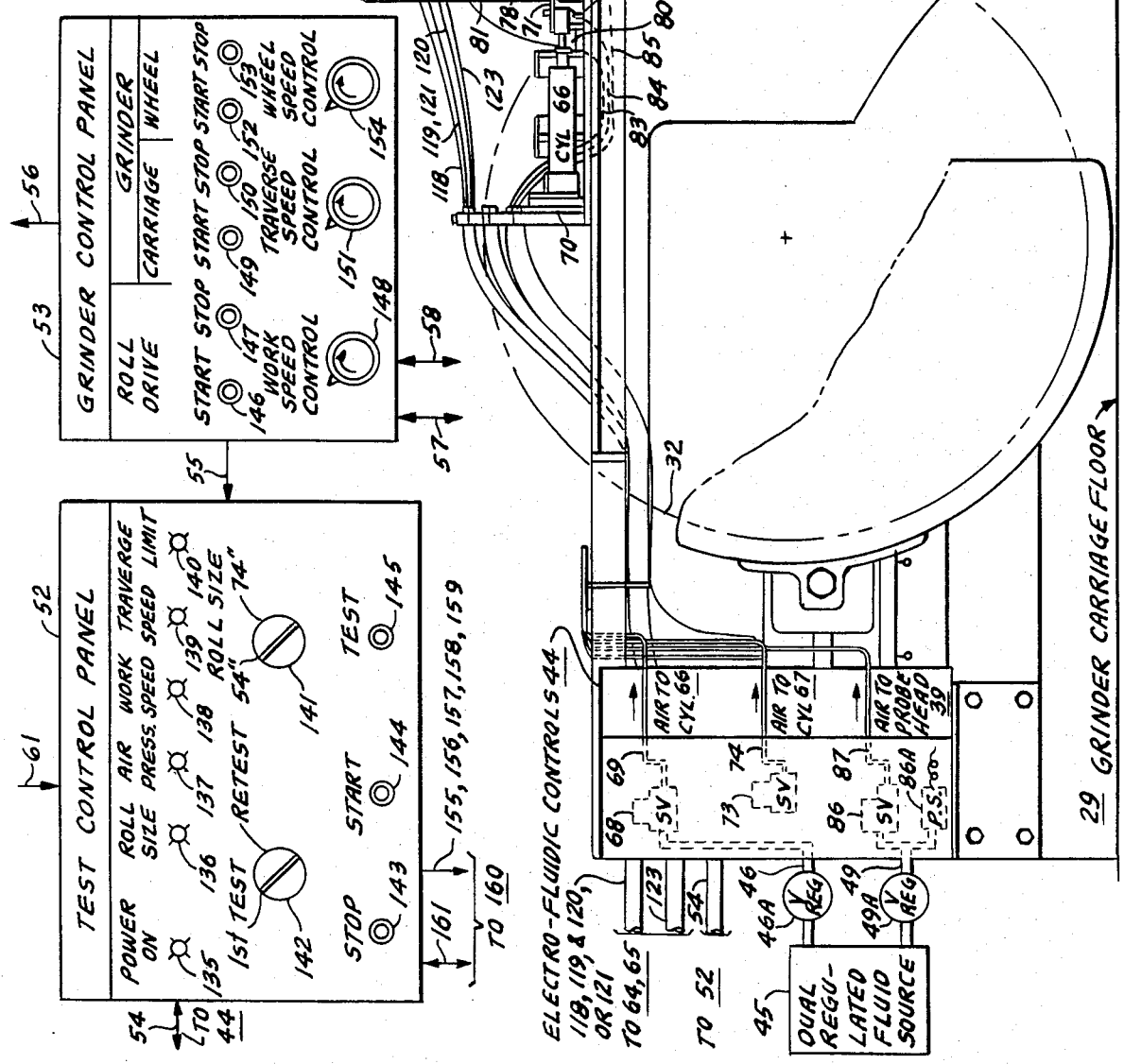

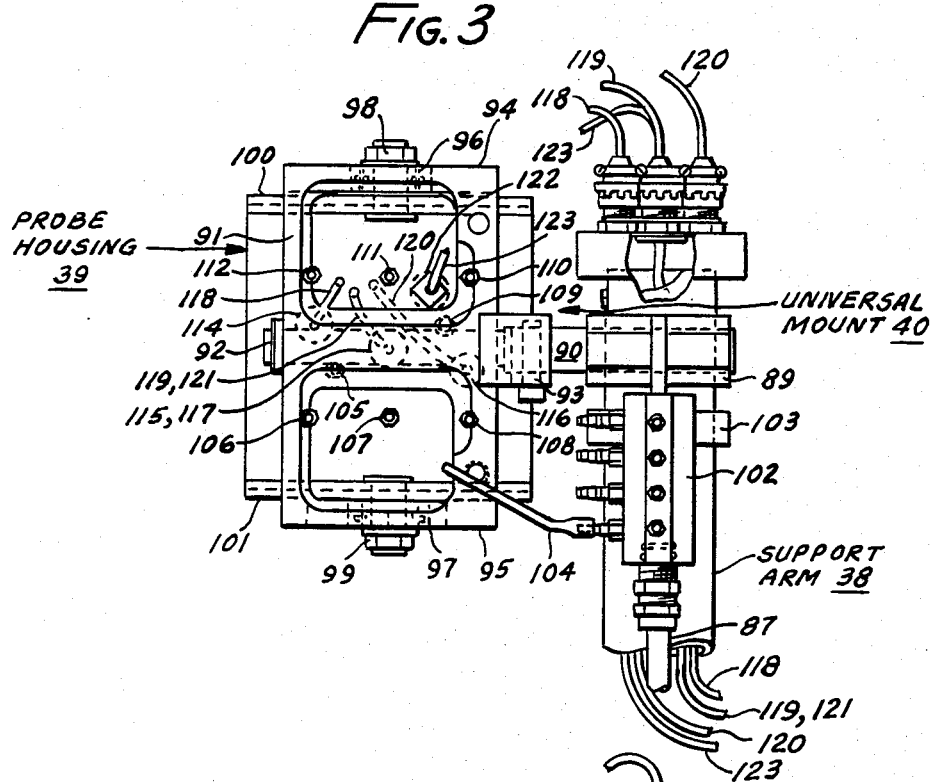
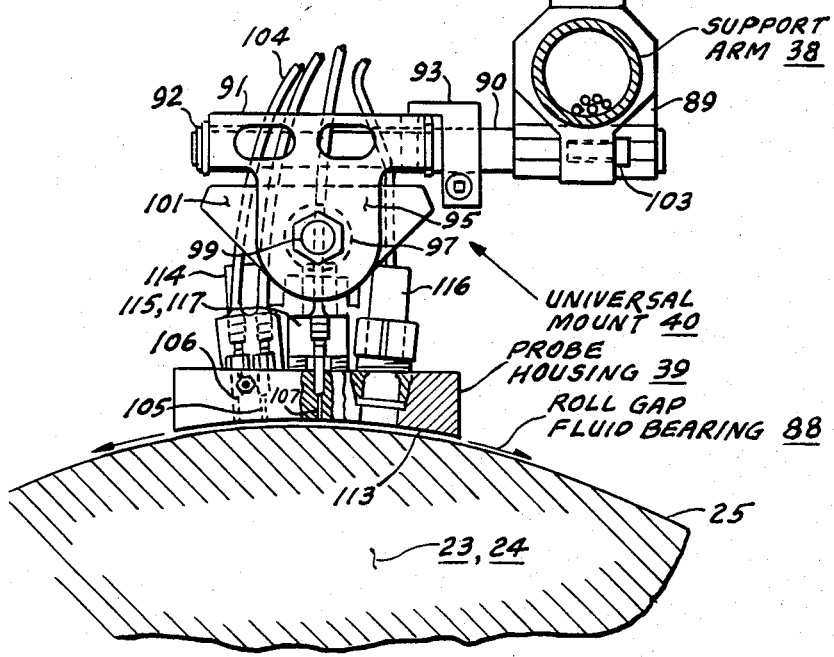

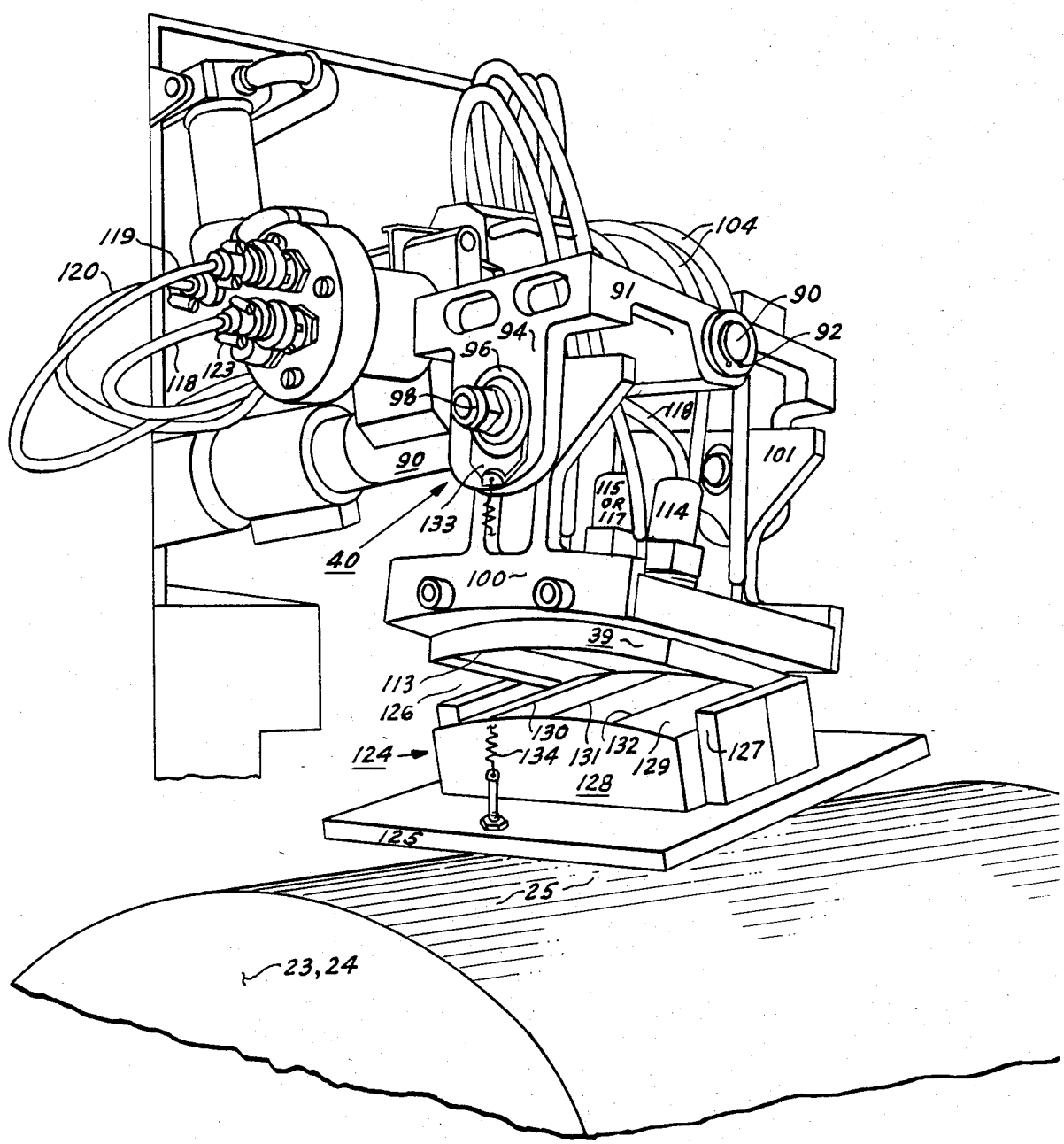

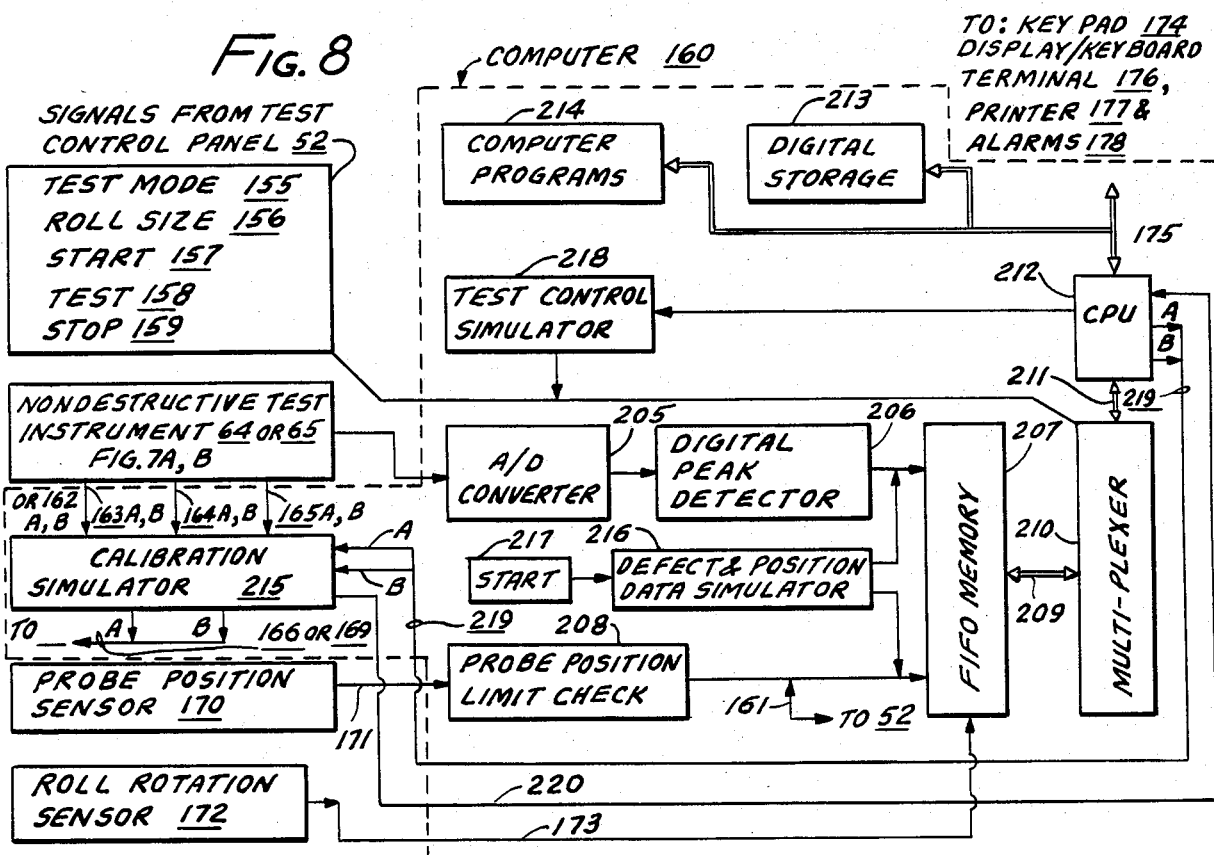

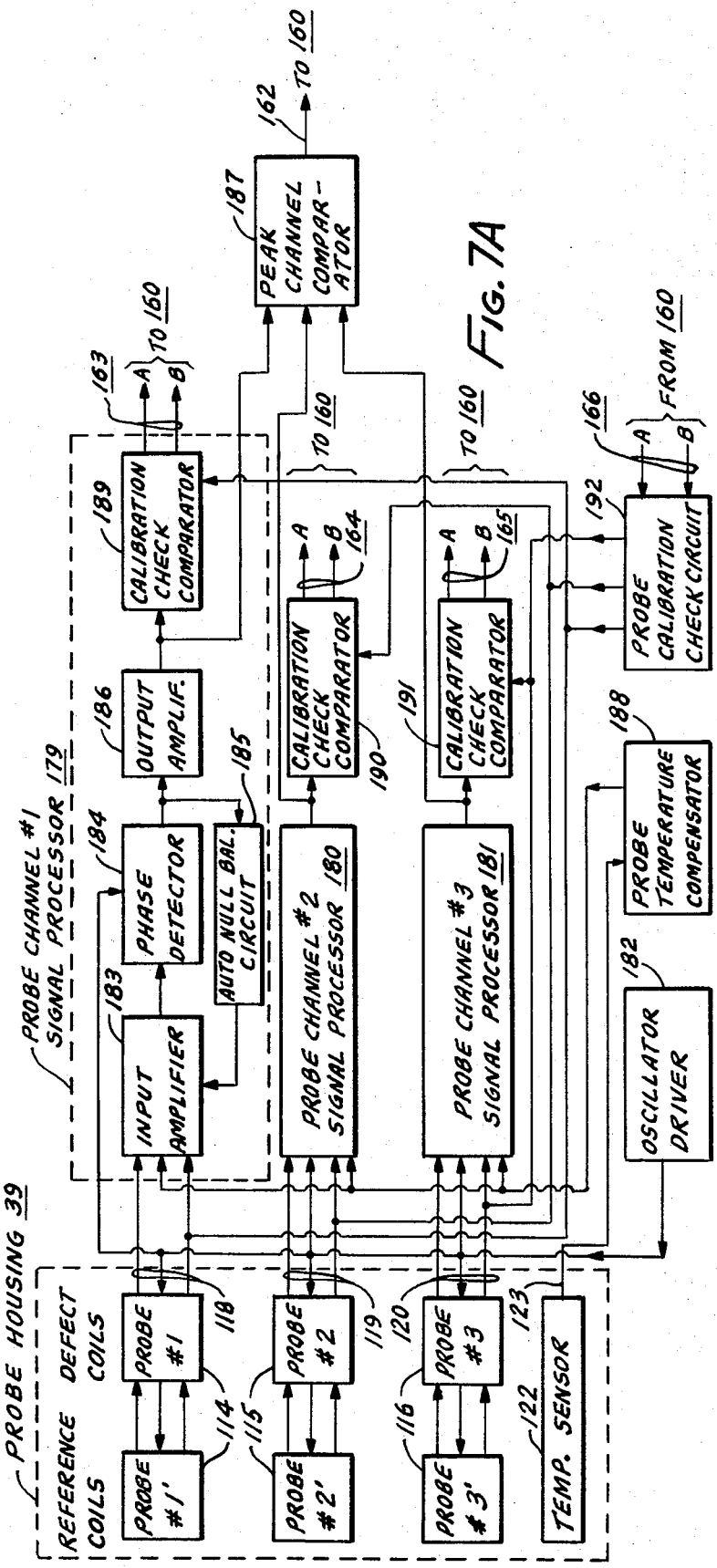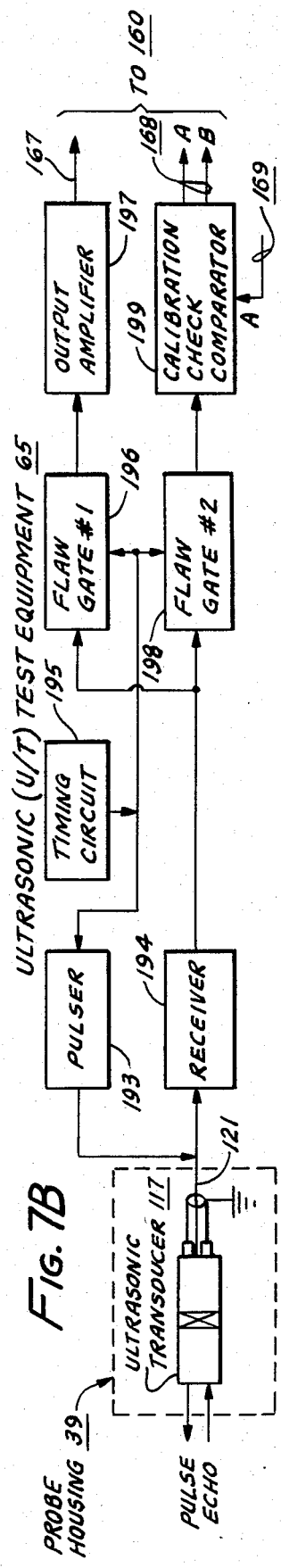

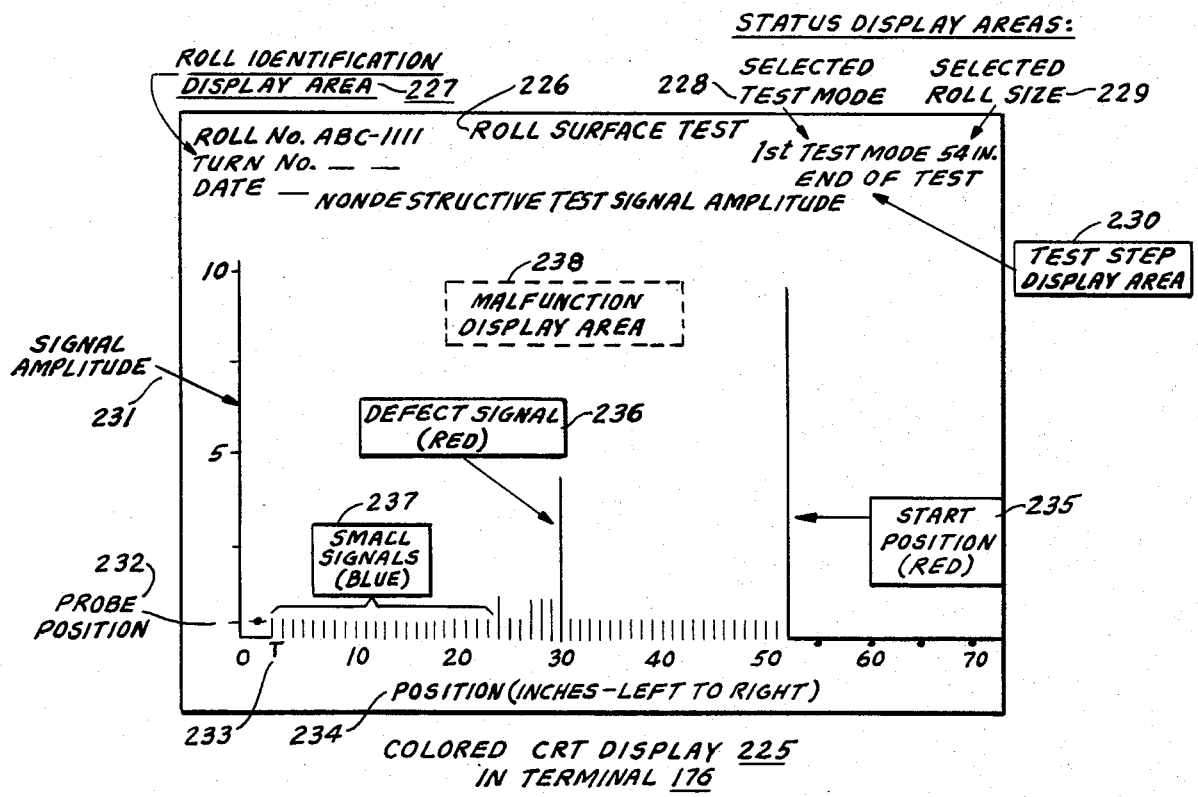

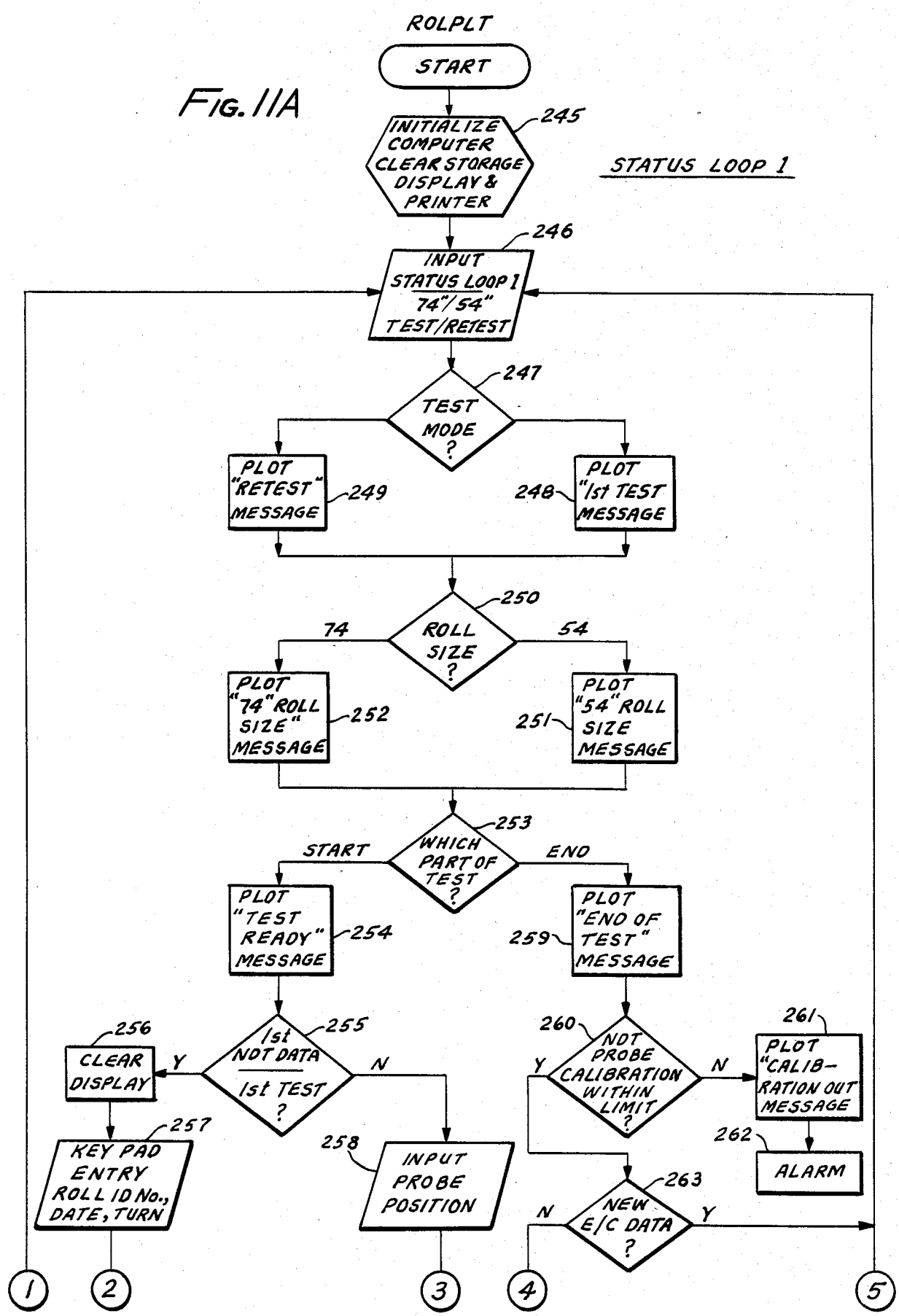

PRBCAL-PROBE CALIBRATION
OFF-LINE DIAGNOSTICS

POSTST-POSITION SENSOR
OFF-LINE DIAGNOSTICS

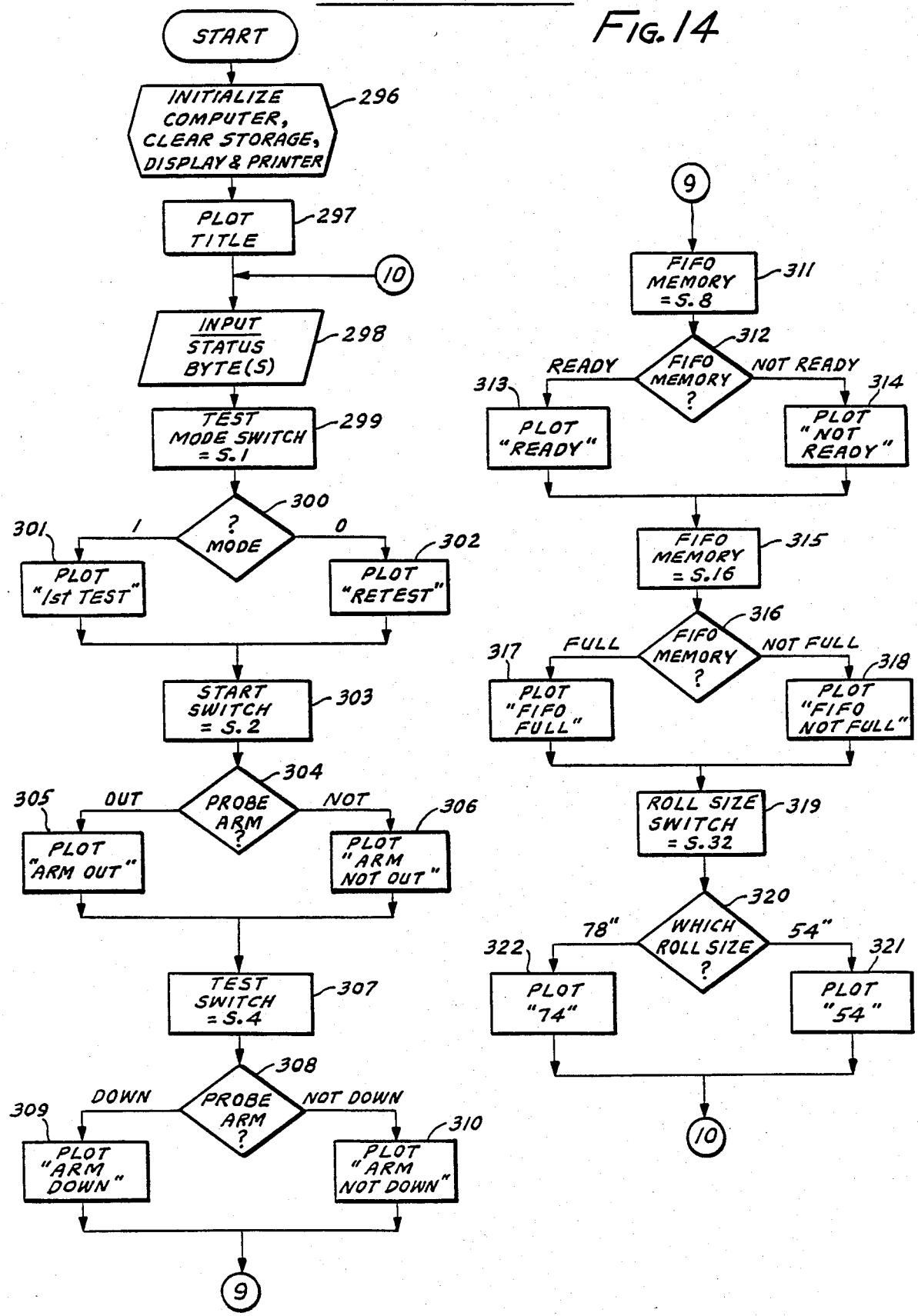

AUTOMATIC NONDESTRUCTIVE ROLL DEFECT INSPECTION SYSTEM

BACKGROUND OF THE INVENTION

This invention relates to a computer-based nondestructive eddy current or ultrasonic testing system for automatically inspecting rolling mill roll surfaces for defects during a rolling mill roll grinding operation by grinder personnel, and others, who ordinarily are unskilled in nondestructive testing (NDT) methods.

DESCRIPTION OF THE PRIOR ART

Cast and forged steel rolls used in high-speed tandem rolling mills to make flat steel products, for example, represent a significant part of procurement and maintenance costs of these mills. Mill records show that theoretical roll availability is reduced by as much as fifty percent before such rolls fail or have to be scrapped. Observations of failed tandem mill rolls indicate many failures originate at surface damage not visually detected by a grinder operator and removed during normal reconditioning. In a tandem mill environment, roll failure is caused by surface spalling and radial shelf cracking type of defects.

Spalling and shelf cracking defects in rolls are caused by a combination of high end pressures, wear conditions, work hardening and internal hardness variations. Such conditions may arise in production operations from untrimmed butt welds and laminations passing through tandem mills; secondary damage from debris of another roll failure; unusual mill operations that overstress the roll surface; or improper off-line handling. Oftimes, rolls subject to spalling and cracking defects are prematurely scrapped when reground to remove such defects and reused only once or twice in a mill after an accident.

Rolls with surface spall and crack defects make an unwanted impression on the surface of the rolled product. This condition is cause for scrapping of the rolled product, as well as for more frequent roll changes and roll surface grinding. All of these situations cause expensive downtime delays and adversely affect mill output and profitability.

Presently, the most common method of detecting rolling mill roll surface defects, whenever they occur, is visual observation of the roll surface by a grinder operator at an off-line roll grinder station. Normally, a grinder operator may not observe surface crack defects as small as about ⅛ inch long and 0.020 inch deep which should be classified as unacceptable to prevent roll failure. Oversight of unacceptable defects with this visual method is a serious problem and must be overcome if mill output and profits are to be increased.

Some attempt has been made to use laboratory types of nondestructive (NDT) eddy current or ultrasonic test instruments in a steel rolling mill environment at an inspection station aside from the roll grinder station with only limited success. Such test apparatus includes a simple uncompensated eddy current test probe, for example, which is manually adjusted so that a wearing block at the probe end will contact the roll surface and attempt to maintain a constant roll gap while the probe traverses the roll surface. Probe output signals are sensitive to roll gap undulations, wearing block noise, probe ambient temperature and roll metallurgy and hardness variations, as well as the roll surface defects to be detected. Thus, the probe outputs a complex analog test signal pattern to a conventional non-destructive eddy current or ultrasonic test instrument, which does not compensate for the variables added to the analog defect signal, and the prior art apparatus plots the complex analog test signal vs. probe position simply on an oscilloscope and/or recorder.

The prior art complex analog test signal pattern plot and setup must be processed in a test instrument and evaluated by a separate inspector skilled in NDT test and analysis methods. This must be done while the roll is at the inspection station in order to ascertain roll surface defect characteristics among the complex test pattern. After an interpretation of the plot is made, the test roll must be transferred back and forth between roll inspection and roll grinding stations, then reinspected until the roll surface is acceptably reconditioned or the entire roll is discarded. This arrangement of test, grind and retest is not only an expensive test method, but it consumes a lot of extra production down time as well. In addition, it also requires an inspector or test operator to be skilled in NDT test and analysis processes. Commercial test equipment for automatically detecting roll surface defects is unavailable.

SUMMARY OF THE INVENTION

An object of this invention is to provide an improved nondestructive eddy current or ultrasonic testing system for automatically inspecting rolling mill roll surface for defects.

Another object of this invention is to provide an improved nondestructive eddy current or ultrasonic testing system for determining roll surface defects without requiring a roll test operator to possess nondestructive (NDT) test or analysis skills, yet improve test performance, test time and measurement accuracy.

Another object of this invention is to provide an improved nondestructive eddy current or ultrasonic testing system for determining roll surface defects without requiring a roll test operator to manually adjust test probe position to obtain valid test signals and results.

Still another object of this invention is to provide an improved nondestructive eddy current or ultrasonic testing system for determining roll surface defects which permit defect detection and roll grinding operations to be carried out without interchanging a test roll between roll test inspection and roll grinding stations.

Yet another object of this invention is to provide an improved nondestructive eddy current or ultrasonic testing system for determining roll surface defects which automatically compensates test probe signal for variations caused by other than defects.

It is yet another object of this invention to provide an improved nondestructive eddy current or ultrasonic testing system for determining roll surface defects which includes novel defect display and equipment diagnostic capabilities.

The foregoing objects are attained by providing a computer-based nondestructive eddy current or ultrasonic testing system for automatically inspecting rolling mill roll surfaces for defects during grinding operations comprising an articulated probe mechanism, a nondestructive eddy current or ultrasonic test instrument means, operator control means, computer means and display and printer means. The articulated probe mechanism is mounted on a traversing roll grinder carriage in line with the grinding wheel, is automatically positioned over the test roll at the grinding wheel in response to the control means initiated by the grinder operator, and has a probe head with a controlled fluid bearing, air or liquid, to automatically maintain probe head-to-test roll gap, thereby avoiding a roll gap wearing block. One or multiple nondestructive eddy current or ultrasonic test probes in the test head generate anomaly test signals which, together with a probe head temperature sensor signal, are processed in a modified nondestructive eddy current or ultrasonic test instrument and the computer In their combination, compensation is made to automatically condition, null and calibrate for variables other than defects. The computer also plots defect signals as color bars vs. probe position and displays these bars graphically, and other messages, on a color CRT display and/or a graph printer. The computer provides diagnotic means for determining equipment status.

This system arrangement provides for effective roll surface defect inspection at the grinder station by grinder personnel, and others, who ordinarily are unskilled in NDT test and analysis methods, yet improves test performance, test time and measurment accuracy, compensates for test probe signal variations other defect signals, and is carried out without interchanging test rolls between roll test inspection and roll grinding stations.

BRIEF DESCRIPTION OF THE DRAWINGS

FIG. 1 is a plan view block diagram of the overall computer-based automatic nondestructive test system of the overall invention showing the articulated probe mechanism mounted on a roll grinder carriage, over a test roll, controls for automatically positioning the probe mechanism over the roll, a nondestructive eddy current or ultrasonic test instrument, the computer means, display and printer means, and grinder, grinder carriage, and test roll drive means.

FIG. 2 is an elevational view of the articulated probe mechanism of this invention mounted on a grinder carriage and including schematic electrofluidic connections thereto.

FIG. 3 is an enlarged plan view of the probe head portion of this invention.

FIG. 4 is an enlarged lateral cross-sectional view of the probe head at a test roll surface.

FIG. 5 is an isometric view of the probe head, including a mechanical artificial probe calibrator.

FIG. 6 covers pictorial elevation views of test control and grinder operator control panels for automatically controlling the position of the probe mechanism over the test roll.

FIG. 7A is a block diagram of the probe head sensors and a modified eddy current type of nondestructive test instrument useable with a system computer.

FIG. 7B is a block diagram of the probe head senors and an ultrasonic type of nondestructive test instrument useable with a system computer in lieu of the FIG. 7A embodiment.

FIG. 8 is a block diagram of computer hardware which combined with software cover the computer control functions of the system arrangement of this invention.

FIG. 9 is an illustration of the computer-driven color CRT display means showing a bar graph of roll surface defects vs. probe position computer plot and other message areas controlled by the computer.

FIG. 10 is an illustration of the computer-driven printer means showing a hexidecimal computer plot of defects at various probe positions and other messages determined by the computer.

FIG. 14 is a flow chart of the computer software covering status signal check in an off-line diagnostics subroutine.

DESCRIPTION OF THE PREFERRED EMBODIMENTS

Figure 11B:
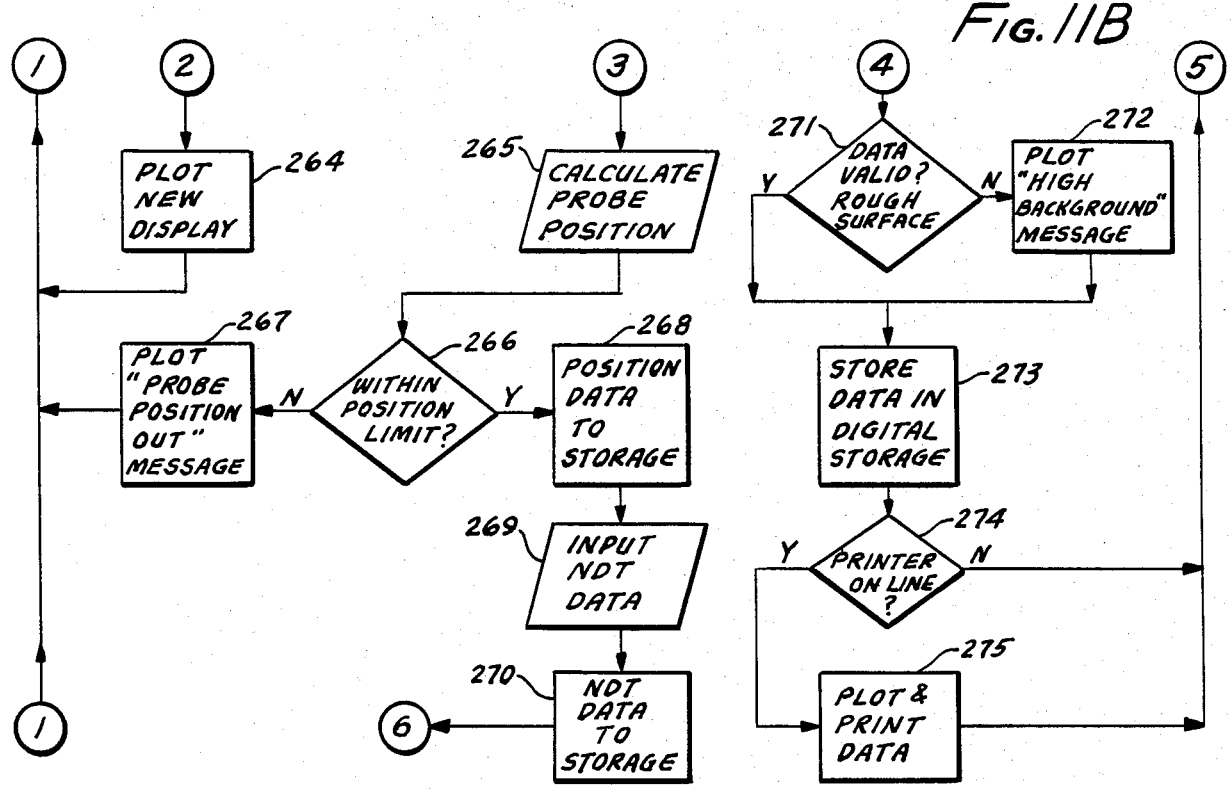
FIGS. 11A,B are flow charts of the computer software covering a roll plot with a first status loop program.

Referring to the drawings, particularly FIGS. 1–6, there is shown the automatically controlled articulated probe mechanism portion of the computer-based nondestructive (NDT) eddy current or ultrasonic testing system for automatically inspecting rolling mill roll surface for defects. The term "nondestructive testing (NDT)" used herein applied to both well known eddy current and ultrasonic test and analysis methods. Similarly, the term "fluid bearing" applies herein to both air and liquid roll gap media.

FIG. 1 shows a plan view in block diagram form of a typical rolling mill roll grinder station 20 where roll lath 21 is operatively associated with roll grinder 22 in both testing and grinding of either 137 cm. (54") or 188 cm. (74") long test rolls 23,24, respectively, around the circumference and lengthwise of test roll surface 25. Roll lathe 21 includes a variable-speed head stock with drive motor 26 under control of roll drive motor controller 27, and further includes a tail stock spindle 28 adjustable to hold either test roll.

Roll grinder 22 includes traversing grinder carriage 29 is driven parallel to the longitudinal axis of test rolls 23,24 by grinder carriage traverse drive motor 30 in response to grinder carriage traverse controller 31. A conventional roll grinder 22 is used which includes a grinding wheel 32 powered by variable-speed grinder drive motor 33 and is controlled by grinder motor controller 34. Grinder drive motor 33 is mounted on the floor of traverse carriage 29 in such manner that grinding wheel 32 may be engaged with the test roll surface 25 throughout the length of either test roll 23,24 while the grinder carriage 29 traverses either right-to-left or left-to-right as shown.

Also mounted on the traversing grinder carriage 29 in line with roll grinding wheel 32 is articulated probe mechanism 35 which is automatically positioned with constant fluid bearing roll gap over test roll surface 25 as shown more clearly in FIGS. 2–6. Articulated probe mechanism 35 comprises a base 36, an upright spindle 37 affixed rotatably to base 36, an articulated support arm 38 pivotally attached to rotatable spindle 37, and a probe housing 39 attached through universal mount 40 to the end of support arm 38 so as to be in line with grinding wheel 32 during testing and grinding operations.

Articulated support arm 38 and probe housing 39 are automatically powered to rotate from safe retracted position 41, shown dotted in FIG. 1, to probe test up position 42 and probe test down position 43, all being done by two pressurized fluid cylinders shown in FIG. 2 and described below. Fluid pressure for these cylinders and the roll gap fluid bearing is controlled by three solenoid valves in electro-fluid controls 44 which is fed from dual regulated fluid source 45. A first regulated pressurized fluid cylinder source is supplied over line 46 to two solenoid valves in control device 44 and then over lines 47,48 to the two fluid cylinders that provide probe support arm 38 movements. A second and separately regulated fluid bearing source is supplied over line 49 to the third solenoid valve in control device 44 for delivery to the probe head-to-roll gap fluid bearing. All fluidic devices will be described more fully below. Limit switches (not shown) in the articulated support arm 38 operate with predetermined movements and provide electrical control signals over line 51 to control device 44 as will also be described below.

Test control panel 52 and grinder control panel 53, both shown in FIG. 6, provide a control and indication means for roll grinder 22 operator to interact with electrofluidic controls 44 over respective control leads 54,55 to initiate automatic controls over testing functions described below. Grinder control panel 53 provides variable speed control signals over line 56 to roll drive motor controller 27, variable speed control signals over line 57 to grinder motor controller 34, and variable speed control signals over line 58 to grinder carriage traverse controller 31, all to provide conventional speed and startstop control functions for their respective powered devices. Grinder carriage 29 traverse is limited according to preselected roll size, either by 137 cm. (54") limit switch 59 action or by 188 cm. (74") limit switch 60 action, both limit switch control signals fed over line 61 to test control panel 52 and on to grinder control panel 53.

As will be described below, articulated probe mechanism 35 has a probe housing 39, one to three nondestructive testing (NDT) probe sensors of either the eddy current type or the ultrasonic type, depending on the user's choise and preference. Also included in probe housing 39 is a temperature sensor. Separate anomoly test signal path(s) and temperature signal path emanate from probe house 39 and are fed over respective lines 62,63 to an appropriate nondestructive test instrument 64,65. Such a test instrument may be of conventional eddy current or ultrasonic 64,65 design. Or test instrument 64,65 may be modified as shown in the block diagrams of FIG. 7A,B described below.

Turning now to FIGS. 2 to 5, articulated probe mechanism 35 is automatically positioned relative test roll surface 25 by two pressurized fluid power cylinders 66,67 acting against structural components thereof to cause movement. Fluid lines have been omitted for purposes of clarity. Fluid cylinder 66, under control of solenoid valve 68, receives first source 46 cylinder regulated fluid pressure over pipe 69 and acts against stationary butt plate 70 and bellcrank 71 on spindle 37 to cause spindle 37 and articulated support arm 38 to rotate about spindle vertical axis 72. When fluid cylinder 66 is extended, articulated support arm 38 is rotated 90° to the safe retracted position 41 shown in FIG. 1 but not FIG. 2, support arm 38 being in the probe test up position 42. When fluid cylinder 66 is retracted, articulated support arm 38 is rotated to the probe test up position 42 shown in FIG. 2.

Fluid cylinder 67, under control of solenoid valve 73, also receives first regulated pressurized fluid cylinder source 46 preset by valve 46A over pipe 74 and acts against yoke 75 bolted onto spindle 37, through arm height adjustment line 76, forked arm end 77 and fork pin 78 to raise and lower the position of arm axis 79 between probe test up position 42 shown dotted and probe test down position 43 shown solid in FIG. 2. When fluid cylinder 67 is retracted, articulated probe support arm 38 is in the probe test up position 42, shown dotted in FIG. 2, and when extended arm 38 is in the probe test down position 43.

Fluid cylinder 66,67 travel distance is controlled by two corresponding limit switches 80,81, respectively, which provide electrical control signals over leads 83,84 to the coils of solenoid valves 68,73 in electro-fluidic controls 44. Limit switch 80 is adjusted so that cylinder 66 rotates spindle 37 90° between the safe retracted position 41 of articulated support arm 38 and the probe test up position 42. Limit switch 81 is adjusted so that cylinder 67 raises and lowers the articulated support arm 38 in the test position between up and down probe test positions 42,43, respectively.

When the articulated support arm 38 is in the probe test down position 43, a third limit switch 82 provides an electrical control signal through leads 85 to solenoid valve 86 which controls the on-off flow of the second regulated pressure fluid bearing supply 49 over pipe 87 to probe housing 39. The amount of second regulated pressure for the fluid bearing is preset at regulating valve 49A by the grinder operator so as to maintain a constant predetermined dimension at roll gap fluid bearing 88 between probe housing and test roll surface 25. Pressure switch 86A provides a fluid pressure electrical indicator signal over conduit 54 to test control panel 52 described below.

FIGS. 3–5 show the detailed construction of probe housing 39, and universal mount 40 at the end of articulated support arm 38 which enables probe housing 39 to automatically maintain a uniform dimension in fluid bearing roll gap, regardless of irregularities in test roll surface 25 or those they may be caused by the grinder carriage traverse relative test roll surface 25.

Universal mount 40 has three-degrees of slip and rotational movement for attaching probe head 39 to the end of support arm 38. Included in universal mount 40 is a positioning clamp 89 for presetting an arcuate support position around the end of a tubular member of support arm 38. Extending laterally from position clamp 89 is support shaft 90 slip fitted through a bearing hole (not shown) through the top of an inverted hollowed out U-shaped joint member 91 and held on rotatably by snap ring 92. U-shaped joint member 91 rotation on shaft 90 is limited to a predetermined arcuate movement by stop clamp 93.

Downward extending flanges 94,95 on member 91 contain ball bearings 96,97, respectively, through which nut and bolt assemblies 98,99 provide for arcuate movement thereabout at 90° to the shaft 90-member 91 rotation movement, thus furnishing the second degree of freedom of movement. Probe housing 39 is provided with upwardly extending flanges 100,101 located inside flanges 94,95, respectively, and having an end slidably adapted to be pivotally secured to bolt heads of assemblies 98,99, respectively, thus providing vertical adjustment capabilities as the third degree of freedom of movement of probe housing 39.

The fluid bearing for probe housing 39 is provided by extending fluid bearing regulated pressure pipe 87 to eight-port manifold 102, which is held on the end of support arm 38 by clamp 103. Each outlet on manifold 102 is connected typically through flexible tubing 104 to eight fluid ports 105 to 112 bored through probe head 39 perpendicular to arcuate test surface 113 to communicate with test roll surface 25. Arcuate test surface 113 is machine contoured to match the radius of test roll surface 25 plus a predetermined dimension equal to roll gap fluid bearing roll 88. If during testing any tilting of probe head 39 should occur, a stop cock (not shown) may be connected in each flexible tubing at manifold 102 and adjusted so that individual fluid flow to each fluid port 105-112 when properly balanced will automatically maintain the predetermined dimension uniformly throughout roll gap fluid bearing 88. Maintaining this uniform roll gap is an important parameter in non-destructive testing whether using either eddy current or ultrasonic NDT methods if accurate and reliable results are to be obtained using probe housing 39 or other designs. Nevertheless, the roll gap fluid bearing 88 is a superior arrangement compared to prior art wearing block used therein.

When probe mechanism 35 is automatically positioned over test roll surface 25 as described above, the one-to-three NDT probe sensors therein are each capable of generating an anomaly test signal when detecting defects in test roll surface 25 as roll 23,24 is rotated. Probe housing 39 is shown having NDT probe sensors 114,115,116, each of which are threadably secured in staggered bores drilled on separate axis having the same radius as that of test roll surface 25 to be inspected. Each NDT probe sensor 114,115,116 corresponds to probe channel No. 1,2,3, respectively, and may be of eddy current design to operate with NDT test instrument 64. Each such eddy current probe 114,115,116 may have a single sensor coil located near arcuate test surface 113, or may have on additional reference coil spaced away from surface 113.

Alternatively a single utlrasonic probe sensor 117, located in probe housing 39 at the same bore as eddy current probe sensor 115 and arcuate test surface 113, may be operatively associated with NDT test instrument 65. Ultrasonic probe sensor may be of a single alternate transmit/receive crystal design or have dual crystals to perform separate transmit and receive functions. Both types of eddy current and ultrasonic probe sensors and corresponding NDT test instruments are described below with reference to FIGS. 7A,B descriptions.

Eddy current type of probe sensors 114,115,116 each generate an eddy current anomoly test signal characterized by a complex analog signal waveform representing a test roll surface 25 defect anywhere along a circumferential scanning path along test roll surface 25. These eddy current anomaly test signals are fed over corresponding lines 118,119,120 to NDT test instrument 64. Similarly, ultrasonic probe sensor 117 generates an ultrasonic anomaly test signal characterized by a variable amplitude pulse signal representing a test roll surface 25 defect as with the eddy current probes. The ultrasonic anomaly test signal is alternately fed over line 121 to NDT test instrument 65.

In some installations the ambient temperature of probe housing 39, roll gap fluid bearing 88 and/or test roll surface 25 may vary beyond calibration or other acceptable limits, particularly on test roll surface 25 during or immediately after roll grinding procedures. For these reasons, probe housing 39 is also provided with probe temperature sensor 122 located adjacent the probe sensors 4,115,116 or 117. Probe temperature sensor signal is fed over line 123 to compensate a modified NDT test instrument 64,65 for variations in the corresponding anomaly test signals due to such temperature variations. Otherwise, if any of the aforesaid temperature variations does not significantly affect defect test signals, then temperature sensor 122 and line 123 may be eliminated from probe lead Turning to FIG. 5, there is shown in isometric view the component parts of probe housing 39 and universal mount 40 located at the end of support arm 38, Provisions are also shown for artificial calibrator 124 to be inserted at arcuate test surface 113 in place of test roll 23,24, adjacent their roll test surface 25. Artificial calibrator 124 has a rectangular flat base 125, two upright members 6,127 at opposite sides of base 125, and a cast steel roll segment 128 secured to and between upright members 126,127 and to base 125. Cast steel roll segment 128 has the same metallurgy as rolls 23,24 and is machined with an artificial arcuate test surface 129 to correspond to the contour of test roll surface 25 radius. Machined in artificial test surface 129 are three test grooves 130,131,132 of known characteristic defect and these grooves correspond to the location of NDT probe sensors 116, 115 or 117, 114 shown in FIG. 3. Artificial calibrator 124 is held with artificial arcuate test surface 129 against arcuate test surface 113 in probe housing 39 by a pair of attachment clips 133 with an opening slipped over each nut end of device 98,99 and held biased in position with two attachment springs 134. After artificial calibration procedures are completed, calibration device 124 is removed from probe head 39.

Not shown is a shim of the same dimension as roll gap fluid bearing 88 which is placed between the two arcuate test surfaces 113 and 129. This is done to completely duplicate as near as possible a probe calibration setup resembling actual roll test conditions. The use of artificial calibrator 124 is a preferred embodiment for calibrating the entire computerized NDT testing system.

Reference will now be made to FIGS. 1 and 6 for the description of test control panel 52 and grinder control panel 53, both of which are provided so that the grinder operator may perform the NDT testing of rolls 23,24 without having any skills in these methods of testing. Test control panel 52 includes a series of indicator lights 135-140 that indicate the sequential status of respective functions including 135 test power on, 136 roll size selection mode, 137 fluid bearing pressure on, 138 roll 23,24 up to preset work speed, 139 grinder carriage 29 up to preset traverse speed and 140 grinder carriage 29 traverse at preselected roll size as determined by limit switches 59,60. Test control panel 52 also includes roll size selector switch 141 having 137 cm. (54") and 188 cm. (74") preset positions, and a test mode selector switch 142 having IST TEST and RETEST preset positions, both of which are preset by the grinder operator before automatic testing may proceed.

Test control panel 52 includes three pushbuttons for the grinder operator to initiate internal control devices, which together with solenoid valves 63,73,86 in electro-fluid controls 44, cooperate to automatically position probe mechanism 35 over test roll surface 25 and maintain roll gap fluid bearing 88 as described above. STOP pushbutton 143 will interrupt and stop a test procedure at any sequential step and deenergize solenoid valves 68,73,86 so that fluid cylinders 66,67 return articulated support arm 38 to the safe retracted position 41 with probe housing 39 in the probe test up position 42 when retracted, fluid bearing flow is stopped in probe housing

39. START pushbutton 144 reenergizes solenoid valve 68 and causes fluid cylinder 66 to swing articulated support arm 39 90° to the probe test up position 42. TEST pushbutton 145 energizes solenoid valve 73 and causes support arm 38 to lower to horizontal probe test down position 43. At the time support arm 38 reaches the probe test down position 43, solenoid valve 86 is energized and causes the fluid bearing flow to appear at probe head 39 when in the test down position 43. This automatically establishes the predetermined dimension of roll gap fluid bearing 88 and prepares for defect detection along the portions of roll test surface 25 to be inspected. Support arm 38 may be raised to the probe test up position 42 for roll inspection or other purposes and the fluid bearing flow ceases by pressing START pushbutton 144. A return to the testing position will be accomplished thereafter by again pressing the TEST pushbutton 145.

Grinder control panel 53, which interacts with test control panel 52, includes only those control functions associated with grinder operator controls that are required for explanation of the present invention, but not necessarily all grinder control function avaiable to the grinder operator. Roll drive START and STOP pushbuttons 146,147 and work speed control preset rheostat 148 provide corresponding control and variable speed control signals on line 56 to and from roll drive motor controller 27. Grinder carriage START and STOP pushbuttons 149,150 and traverse speed control preset rheostat 151 provide corresponding control and variable speed control signals on line 58 to and from grinder carriage traverse controller 31. Grinder wheel START and STOP pushbuttons 152,153 and wheel speed control preset rheostat 154 also provide corresponding control and variable speed control signals on line 57 to and from grinder motor controller 34.

Also included in grinder control panel 53 are the source of indicator signals fed over line 55 to test control panel 52 for roll work speed indicator 138 and traverse speed indicator 139 when their respective drive controllers 27,31 have caused their drive motor to reach the speed preset by rheostats 148,151. The traverse limit indicator 140 on test control panel 52 lights up when grinder carriage 29 reaches limit switch 59 or 60 after being preselected by roll size selector switch 141 also on the test control panel 52.

When the automatic probe positioning procedure is completed to the probe test down position 43, the anomoly test signals generated by eddy current probe sensors 114,115,116, or alternatively the ultrasonic probe sensor 117, representing test roll surface 25 defects, are fed from articulated probe mechanism 35 to nondestructive test instrument 64 or 65 shown in FIG. 1. Similarly, if temperature sensor 122 was included in probe housing 39 with either eddy current or ultrasonic type of test probe sensor, then the temperature signal will be fed separately from articulated probe mechanism 35 to nondestructive test instrument 64,65 shown in FIG. 1. Due to interlocking control functions of control panels 52,53, these anomoly test signal(s) and temperature signal are generated, in probe test down position 43, along the entire length of preselected roll 23,24 when carriage 29 traverses from either right-to-left or left-to-right of the grinder operator, and will continue to be generated until a complete scan is made in one direction of test roll 23,24.

When defects are found on test roll surface 25, either plunge grinding or traverse refinishing of the entire test roll surface 25 will be necessary and require use of grinder apparatus 22 by the roll grinder operator. After this is done, roll surface 25 defect testing may be repeated, if desired, by the grinder operator turning roll test mode selector switch 142 on test control panel 52 to the RETEST position momentarily and repeating the foregoing automatic defect testing and grinding or refinishing procedures the number of times required to accept or reject test roll 23,24. In RETEST mode of defect testing probe housing 39 will automatically return to the test probe test up position 42 when TEST pushbutton is not depressed. Pressing the test STOP pushbutton 143 will automatically return probe housing 39 to the safe retracted probe position 41.

At each step of automatic positioning of probe mechanism 35, test control signals are fed forward, including test mode signal 155 from switch 142, roll size signal 156 from switch 141, start signal 157 from pushbutton 144, test signal 158 from pushbutton 145, and stop signal 159 from pushbutton 143, to computer 160 for use as described below. Computer 160 and test control panel 52 communicate acknowledgement signals on line 161.

Reference will now be made to the computer-based portion of the automatic nondestructive testing system for inspecting rolling mill roll surface for defects as shown in FIGS. 1, 7A, 7B to 15.

The one to three anomaly test signals on lines 118,119 and 120, or 121, together with the probe temperature signal on line 123, all generated by events at probe housing 39, are fed to modified nondestructive eddy current, or ultrasonic, test instrument 64, or 65, respectively, shown in FIGS. 7A, 7B. These instruments process anomaly test signals and the temperature signal, if desired, in one to three individual probe channel circuits including converting anomaly test signals to defect signals, automatic nulling, temperature compensation if desired, selecting the highest defect of multiple test probe channels for processing by computer 160, and/or performing calibration checks on each probe channel circuit in cooperation with computer 160.

Nondestructive eddy current test instrument 64 shown in FIG. 7A selects the highest defect signal from three probe channels and outputs an amplitude-variable analog defect signal on line 162 to computer 160 shown in FIG. 8. NDT eddy current test instrument 64 also outputs three calibration limit check signals on lines 163, 164, 165, to computer 160 and also receives from computer 160 a combination of calibration check control signals on line 166 to check each probe channel calibration. Nondestructive ultrasonic test instrument 65 outputs an amplitude-variable analog defect signal on line 167 and a calibration limit check signal on line 168 to computer 160 and receives from computer 160 a calibration check control signal on line 169.

Since articulated probe mechanism 35 is mounted on grinder carriage 29 and while tests are in progress it traverses over test roll surface 25 at a variable speed, grinder carriage traverse drive motor 30 is provided with probe position sensor 170. This sensor generates a probe position signal on line 171 which is relative to the length of test roll surface 25 traversed by probe mechanism 35. The probe position signal on line 171 is fed to computer 160 which uses same to track probe position, both from right-to-left and left-to-right probe scan directions.

Test roll 23,24 is also rotated by variable-speed drive motor 26 during defect testing and for this reason roll rotation sensor 172 is provided in the drive motor housing so as to generate a roll rotation signal on line 173.

This signal is fed to computer 160 where it represents the circumferential dimension of test roll surface 25 in determining surface location of defects.

The analog defect signals on line 162, or 167, the probe position signal on line 171, and the roll rotation signal on line 173 are all fed to computer 160 shown in FIG. 8 and described below. Briefly, computer 160 is shown providing one of several possible combinations of hardware and software programmed to convert the analog defect signals to digital roll surface defect signals and to process these signals along with the probe position signals. Computer 160 determines and plots a plurality of prescribed amplitude-variable bar signals for every inch (2.54 mm.) of length of test roll 23,24. Each bar signal represents severity of defect on an amplitude scale at a given roll surface location determined by the probe position signal. Computer 160 also plots a probe position pointer to follow an incremental position overlay generated internally. In addition, computer 160 uses the roll rotation signal along to aid in processing the probe position signal and roll defect signal to determine the circumferential location of a defect on test roll surface 25.

Additional functions of computer 160 include probe calibration checks, plotting of operator message areas, status plots, test roll identification plot based on input by key pad 174. Computer 160 additionally communicates through input/output ports 175 to display/keyboard terminal 176, with a format shown in FIG. 9, to printer 177 having another format shown in FIG. 10, and to alarm device 178 which is activated whenever a defect exceeds a preset level. Computer program flow charts for performing certain plotting and diagnostic features are shown in FIGS. 11A,B to 15.

Referring back to FIG. 7A, there is shown a block diagram of a modified eddy current test instrument 64 which may process any one to all three channels of variable-amplitude anomaly test signals, each having a complex analog waveform, in probe channel signal processors 179,180,181. With three probe sensors 114,115,116 in probe housing 39 covering three adjacent signal scan areas of test roll surface 25, the traverse speed of carriage 29 may be three times as fast as for any one sensor, thereby reducing defect inspection time proportionally.

Probe sensors 114,115,115 in probe housing 39 each have a defect coil spaced closely to the test roll surface 25 and connected to oscillator 182 and a differential input amplifier 183 shown in probe channel #1 processor 179. In many large steel mills, for example, there are severe environmental conditions that must be lived with, including variations in test temperatures and the presence of strong electrical fields which may influence unacceptably, the accuracy and performance of electrical test equipment. To deal with test situations, it is desirable to add a reference coil spaced about 3.8 cm. (1½") away from the defect coil, but in the same housing and connected in a bridge circuit with each defect coil driven by oscillator 182. Consequently, the reference coil will tend to compensate probe sensor defect coils against the mill environmental effects.

Probe channel #1 signal processor 179 also includes a phase detector 184 which converts the input amplifier 183 anomaly test signal to an amplitude-variable analog defect test signal. This signal is automatically nulled advantageously in a feedback arrangement with automatic null balance circuit 185 and input amplifier 183. The nulled analog defect test signal is suitably scaled in output amplifier 186 and fed out of processor 179 to peak channel comparator 187. Each probe channel #2 and #3 signal processor 180,181 is the same as processor 179, and each of their nulled analog defect test signals are fed out to the peak channel comparator 187. Here comparator 187 selects the multiple probe channel with th4e highest amplitude defect signal for output on line 162 to computer 160 for digitizing and further processing as an eddy current embodiment of NDT test instrument 64.

In some operating practices, the ambient temperature variation of probe housing 39, of roll gap fluid bearing 88 and/or of test roll surface 25 may have an adverse effect on the overall accuracy or performance of eddy current test instrument 64. If such variations occur, temperature sensor 122 may be incorporated in probe head 39, near the source of temperature variation, and the temperature sensor signal on line 123 fed to probe temperature compensator 188 which applies a correction signal to each input amplifier 183 in probe channel #1,2,3 processor 179,180,181. Consequently each nulled analog defect signal output from their respective output amplifier 186 will also be corrected for test site temperature variations.

A probe calibration check is made of each probe channel #1,2,3, including coils in each probe sensors 114,115,116, the probe channel signal processors 179,180,181. Added to each channel signal processor 179,180,181 is a calibration check comparator 189,190,191, respectively, operating under control of probe calibration check circuit device 192. A calibration reference voltage is applied to probe channel #1 input amplifier and calibration check comparator 189, and then sequentially to probe channels #2,3. This is done by a binary logic control input 166A,B from computer 160 as described below.

If probe sensors and channel processor 179,180,181 gain are satisfactory when compared to the calibration reference voltage, then there will be no output on lines 163A,B, 164A,B, 165A,B, to be fed to computer 160. Otherwise, if the probe calibration check exceeds an upper limit then a high output will appear on line 163A, 164A, 165A which is fed to computer 160. If the probe calibration check exceeds a lower limit, then a high output will appear on line 163B, 164B, 165B, this also being fed to computer 160. When a malfunction occurs in a probe channel, then lines 163A,B, 164A,B, 165A,B, have high outputs fed to computer 160.

In FIG. 7B there is shown a block diagram of a modified ultrasonic test instrument 65 which may be used alternately with the FIG. 7A eddy current test instrument to provide a variable amplitude analog defect test signal for processing in computer 160. A single ultrasonic transducer 117 is substituted in probe housing 39 at a similar location as say eddy current probe sensor 115. Ultrasonic transducer may be of either well known single or dual crystal construction and connected either alternately or sequentially over line 121 first to pulser 193 then to receiver 194. Timing circuits 195 operate on pulser 193 through transducer 117 to generate a pulse echo in test roll 23,24 and initiate a back echo at the location of a defect in roll test surface 25. This impresses a time-delayed amplitude-variable complex anomaly test signal on the input to receiver 194.

Receiver 194 output is fed to a first flaw gate 196 which, under control of timing circuit 195, passes only a simple amplitude-variable defect pulse generated proportional to the flaw echo representing a test roll defect.

Flaw gate, 196, output is conditioned and scaled in output amplifier 197 and fed on line 167 as an amplitude-variable defect test pulse to computer 160 for alternate processing as described below.

A probe calibration check is made of ultrasonic test instrument 65 by incorporating a second flaw gate 198, also controlled by timing circuits 195, to pass the amplitude-variable defect test pulse to calibration check comparator 199. Comparator 199 checks the test pulse amplitude against an internal reference and, when receiving a binary logic control signal on line 169 from computer 160, will test the defect test pulse against predetermine maximum and minimum level limits. Comparator 199 then operates the same as comparators 189,190,191 in FIG. 7A and output combinations of high level and no outputs on lines 168A,B, which calibration check signals are also fed to computer 160.

Although not shown in FIG. 7B, the probe temperature compensation features of FIG. 7A may readily be incorporated in the ultrasonic test instrument 65, if desired. This simply entails mounting temperature sensor 122 in probe head 39, connecting the temperature sensing lead 123 to a device like probe temperature compensator 188, and connecting a suitably scaled correction signal to the input of ultrasonic receiver 194. The same benefits will be gained as in the temperature compensation of eddy current test instrument 64.

Reference will now be made to FIG. 8 block diagram of computer 160 which shows but one of a number of ways of combining hardware and software for carrying out the data processing functions of this invention. Computer 160 may be a self-contained microcomputer structure, or may be a partial structure having shared responsibility of storage and program features with display/keyboard terminal 176 in order to carry out all of the computer functions described below. Regardless of its specific form and arrangement, computer 160 receives the amplitude-variable defect test signals from either test instrument 64, or alternately 65, on lines 162 or 167, a digital roll position signal on line 171 and digital roll rotation signal on line 173, all generated as described above. The amplitude-variable analog defect test signal on line 162, or the amplitude-variable pulse defect test signal on line 167, is converted to digital form in A/D converter 205. The digital defect signal is fed to digital peak detector 206 where a test roll defect signal peak is detected and allocated according to severity in one of sixteen preset digital levels of test roll defect signals and this signal is applied to FIFO memory 207 as one address in a storage map.

The digital probe position signal on line 171 is first tested in a probe position limit checker 208 to determine probe traverse direction and whether or not probe actual position is within either the 137 cm. (54") or 188 cm. (74") roll size signal communicated over line 161 from test control panel 52 shown in FIG. 6. Whenever the digital roll position signal is within limits, the roll position signal is fed to FIFO memory 207 and used in the storage map to coordinate defect signals with probe position for every inch (2.54 cm.) of length of test roll surface 25 until the entire preset roll size is scanned.

The digital roll rotation signal on lead 173 is also fed to FIFO memory 207 where it is used to ripple therethrough the digital roll defect test signal severity at each inch (2.54 cm.) of probe position according to circumferential location of the defect on test roll surface 25. When each full turn of test roll 23,24 rotation is completed, the digital roll defect signal severity and the instant digital incremental probe position signal are dumped on bus 209 to multiplexer 210. This action continues for each test roll revolution until every incremental probe position of preset roll size length is traversed by probe housing 39, either right-to-left or left-to-right of the grinder operator.

Also applied to multiplexer 210 are test signals from test control panel 52. These include test mode signal 155, roll size signal 156, start signal 157, test signal 158 and stop signal 159, all generated by the automatic probe positioning procedure described above.

Multiplexer 210 outputs defect severity and probe position signal data, as well as the test signals from panel 52, on bus 211 to central processing unit (CPU) 212 which in turn directs them to digital storage 213 and input/output bus 175 under control of computer programs 214. Computer programs 214 comprises on-line roll plot of defects having two loops of sub-programs, test display messages, malfunction display messages, and off-line equipment diagnostics covering probe calibration, status signals and probe position sensor, all as shown in FIGS. 11A,B to 15 and as described below.

Additional features hardwired into computer 160 are provided by probe calibration simulator 215, defect and position simulator 216, simulator start pushbutton 217 and test control simulator 218. Probe calibration simulator 215 received a binary logic control signal on line 219A,B from CPU 212 in response to an off-line probe calibration subroutine described below. Simulator 215 produces the binary logic sequential control signals on line 166A,B used by the probe calibration check circuit 192 in eddy current test instrument 64. Each probe calibration high-low limit check signal on lines 163A,B, 164A,B, 165A,B is fed back from eddy current test instrument 64 to simulator 215. A binary in/out of probe calibration signal on line 220 is fed from simulator 215 back to the CPU 212 for use with binary signal on line 219A,B in recognizing which probe channel #1,2,3 was or was not working and in/out of test limits. Any malfunction will cause computer 160 to plot a message as described below.

Defect and position simulator 216 is initiated by a test operator before testing a roll surface by pressing start pushbutton 217 to simulate the defect data function of defector 205 and probe position limit checker 208 data acting on FIFO memory 207. Any malfunction will cause computer 160 to plot a message as described below.

Test control simulator 218, acting under instruction from CPU 212 and a program described below, simulates automatic probe positioning test signals from test control panel 52. Those signals simulated are test mode 155, roll size 156, start 157, test 158 and stop 159, all of which are fed to multiplexer 210 for processing sequentially back into CPU 212 for test and subsequent message display described below.

Computer 160 communicates over input/output bus 175, under control of computer programs 214, to and from key pad 174, display/keyboard terminal 176, printer 177 and alarm device 178 to perform data processing and display or print functions described below. Key pad 174 permits a test operator, in this case the grinder operator, to enter into computer digital storage 213 test roll identification data such as roll number, date and turn or work shift, and other information about the roll, if desired, for use as described below. The alarm device 178 will be activated by a roll plot sub-program when any of the probe channel calibration checks malfunction, or a defect exceeds a predetermined limit.

Display/keyboard terminal 176, or simply terminal 176, includes a modified, limited keyboard for operator interaction with computer 160, such as to load and change stored computer programs 214, call up display plots, and the like. Also included in terminal 176 is a colored CRT display 225 which is shown in FIG. 9 and laid out with various message display areas easily interpreted by an operator unskilled in NDT test and analysis procedures, such as the grinder operator or others, in this embodiment.

Colored CRT display 225 display areas on a yellow background comprise: ROLL SURFACE TEST area 226 exemplifying nondestructive test probe signal amplitude; ROLL IDENTIFICATION DISPLAY AREA 227 where, for example, three letters and four digits provide roll identification data; status display areas: SELECTED TEST MODE AREA 228 indicating whether this display is for 1ST TEST or RETEST mode of operation, and SELECTED ROLL SIZE AREA 229 indicating 54IN. or 74IN. roll size was selected; TEST STEP AREA 230 indicating TEST READY, RUN TEST or END OF TEST (shown); SIGNAL AMPLITUDE bar scale plot 231, with an 0 to 10 graduation marked in the Y-axis, mainly for operator acceptance, as opposed to 15 of the 16 binary discrete defect signal severity levels by which the defect bar plot varies; PROBE POSITION AREA bar scale plot 232, with 0 to 74 one-inch graduations marked in the X-axis; PROBE POINTER PLOT AREA 233 where "T" pointer advances along probe position scale every inch to signify present location of probe head 39, shown at "0" position at end of test; PROBE POSITION DIRECTION AREA 234 indicating probe scale in inches and that the test probe housing 39 moved from LEFT-TO-RIGHT over the test roll surface 25; START POSITION AREA 235 indicating that the 54" roll size was started at the left end and produced a maximum severity false defect at the start of the test, this being unacceptable and shown as a red bar defect; DEFECT SIGNAL AREA 236 indicating that at position 30, namely 24 inches in from the end of the 54" test roll an unacceptable defect produce a red bar of nominally an 8-level defect; SMALL SIGNAL DEFECT AREA 237 indicating in blue bars small surface defects detected, but of an acceptable level; and MALFUNCTION DISPLAY AREA 238 where CALIBRATION OUT, HIGH BACKGROUND or PROBE POSITION OUT and other messages appear because of a test or equipment malfunction implicit in the message and determined by self-diagnostic programs.

Printer 177, driven by computer 160, prints out a defect print out 239 exemplified in FIG. 10 by a different roll test that shown in FIG. 9 display as can be seen from ROLL identifidation line 240 across the top of the printed record. Also the roll size was 74" long indicated in the horizontal line by one dot per inch of probe housing 39 movement across the test roll surface 25. All test roll surface defects in the printed record are based upon a hexadecimal notation system (0 to 9,A,B,C,D,E,F) developed in computer 160 so that only a single-digit printout will be available at each one-inch probe position location across the record. Thus, a first test was run in which the probe housing was dropped into to test roll surface 25 at the third inch in from the end of a 188 cm (74") test roll, this producing B level starting indication at the starting position As probe housing scanned the test roll, it detected defects at adjacent probe positions 60" and 61" going toward the end of a 74" roll. The grinder operator ground the test roll at the 61" location, and through a series of three grinding and retest steps, removed the defect at the 61" location. After a fourth grinding, a fourth retest showed that no defects were present at either 61" or 62" location along the 74" test roll.

Computer programs 214 in computer 160 will now be described by referring to the flow charts in FIGS. 11A,B,12 to 15. Computer 160 does not have an executive program.

Figure 12:
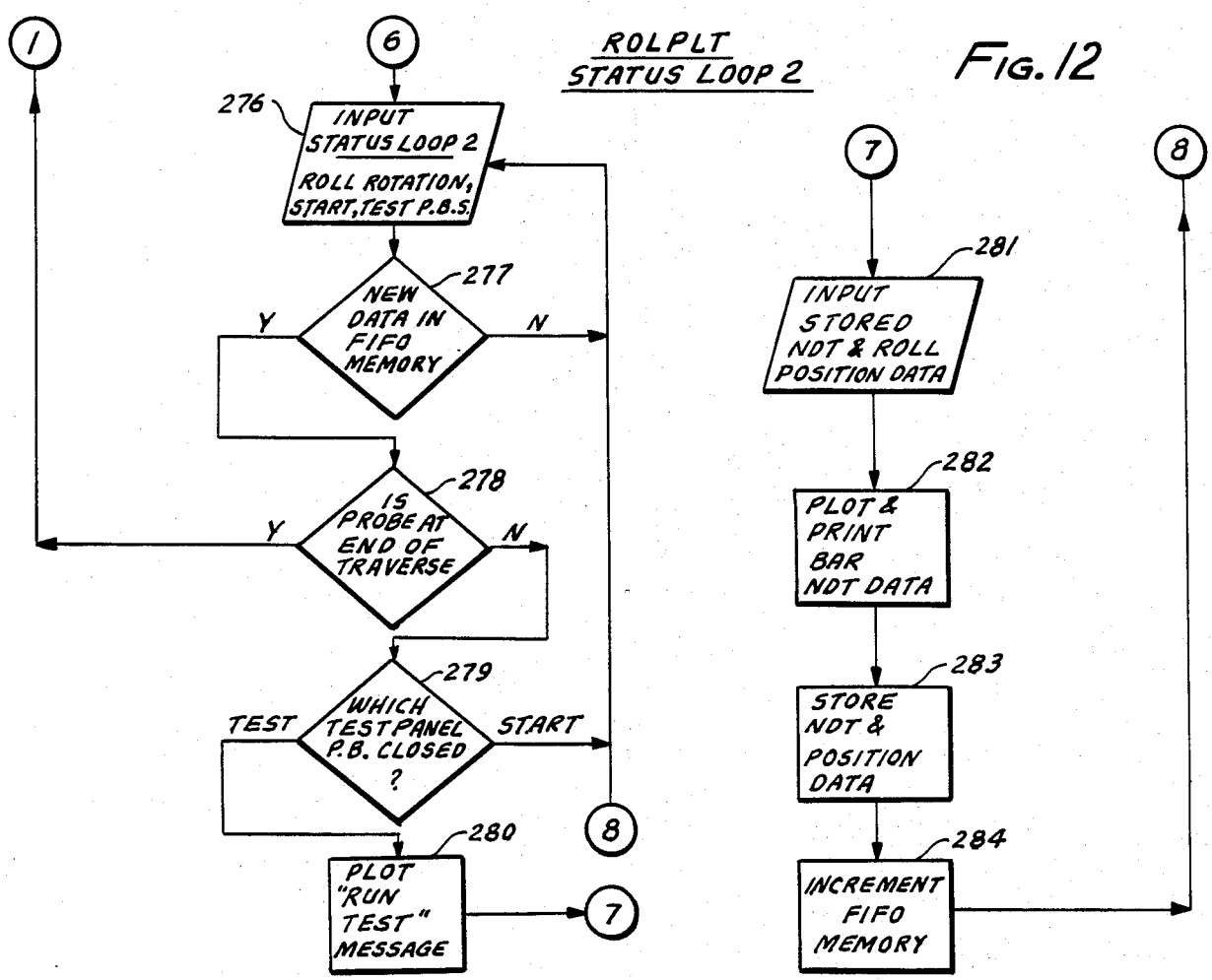
FIG. 12 is a flow chart of the computer software covering a roll plot with a second status loop program.

FIGS. 11A, 11B,12 are flow charts of a Roll Testing program involving a test roll defect plot called ROLPLT having two continuous, interrelated, sub-program loops called STATUS LOOP 1 shown in FIGS. 11A,11B, and STATUS LOOP 2 shown in FIG. 12. STATUS LOOP 1 covers steps 245 to 275 in FIGS. 11A,11B and runs when no testing of roll surface 25 is in progress and probe head 39 is in safe retracted position 41. In other words, probe head 39 has traversed the entire length of test roll surface 25. STATUS LOOP 2 covers steps 276 to 284 in FIG. 12 and runs during roll testing and starts when probe head 39 is in position and START, then TEST signals 157,158 are received in sequence by computer 160. The first part of the ROLPLT program initializes terminal 176 for Roll Testing by setting the CRT graphic variables, clearing interfaces and microprocessor registers and defining program variables, flags and arrays.

STATUS LOOP 1, shown in FIGS. 11A,11B, steps 245 to 275, begins program execution when Status Byte 1 (ST1) is read. The MODE bit is tested to determine if the equipment is set for "1st TEST" of a roll of RETEST of a roll. Then the SIZE bit is tested to determine if the a "54 inch" or "75 inch" roll is being tested. Later the START bit is evaluated to determine if the first step of the two step test procedure has begun. If the "START" bit is LOW the program jumps to the END OF TEST subroutine referred to as (E). The (E) subroutine includes a Rough Surface validation subprogram and a Probe Calibration verification subroutine.

The Rough Surface validation program executes by summing the NDT defect signal amplitudes in array EC(P). Signal amplitudes (EC) at or near the defect threshold $(3>EC<6)$ are combined to obtain a sum (RSX). The sum (RSX) is a running total of the signals EC(P) at 15 consecutive positions (P) along the roll body. If the sum of any 15 consecutive signal amplitudes RSX is greater than the Rough Surface Limit (LRS) the roll surface background signal level is too high for a reliable test, and, a "HIGH BACKGROUND" warning is printed across the CRT display area 238.

The Probe Calibration verification subroutine operates special circuits in the nondestructive instrument 64 or 65 and a data interface at input/output line 175. Computer 160 sequentially generates artificial pulse signals in each of the eddy current probe circuits. A data latch in the interface circuit (not shown) measures the NDT test instrument response to the articifial defect pulse and indicates if the signal was low, on limits, or above preset amplitude limits. Each probe is sequentially pulsed, its response measured and reset. If the signal is outside and the predetermined limits an alarm message indicating "CALIBRATION OUT" and the probe number is written on the CRT display area 238. At the end of the Probe Calibration check subroutine, the program jumps back to the "END OF TEST" program (E). The "END OF TEST" program finishes with Resets of a position counter "0" PCO flag and Traverse Supervisory signal (not shown). The PCO flag is an indicator that tells when a new test is beginning on the 1ST TEST Mode. It is set to zero each time an "END OF TEST" condition occurs and is reset to 1 at the beginning of a Test in the "1ST TEST MODE". Then it loops to the beginning of Status Loop 1 and again executes the same parts of the program.

START OF TEST begins with step 253 when the grinder operator presses his "START" button on the control panel 52, the "START" bit in Status Byte 1 (ST1) indicates start of a test. The PCO flag is tested to determine if a new test is starting. If a new test and the MODE signal is for 1st TEST, the program jumps to the "PLOT CRT DISPLAY" subprogram (not shown). The CRT subprogram erases the entire display, clears the data arrays, and, graphs a new bar plot display on the CRT. The program then loops back to STATUS LOOP 1 and reads Status Byte 1 (ST1) again. This time finding the same status signals with the PCO flag set, the program jumps to the Position P program. In the Position program the low and high Position bytes P(0) and P(1) are read and the probe head position, P, is computed from the roll position signal on line 171.

The program tests the computed probe position P to determine if the probe housing 39 position is within the Head Stock and Tailstock End Limits of the roll body 23,24. If the probe position is outside the limits, the program writes a "POSITION PAST (----) LIMIT" on the CRT display area 238 and resets the traverse Supervisory Signal to disable test control panel 52. This prevents the grinder operator from lowering probe housing 39 when it is outside of the roll body positions.

STATUS LOOP 2, shown in FIG. 12, steps 276 to 284, begins if the "Position" limits are tested affirmative, then the program jumps to the second loop, STATUS LOOP 2, and reads Status Byte 2 (ST2). If the FIFO READY FFR signal indicates data in the FIFO register 207, the program jumps to the POSITION Subroutine P and computes the probe position (P). When the probe position is within the roll body 23,24 limits, the program sets the Supervisory Signal and jumps to a position pointer (PP) program (not shown) that prints a magenta colored pointer "T" at area 233 at the current probe position, P, under the X axis of the CRT display bar graph. From the position pointer (PP) program the execution jumps and the STATUS BYTE 2 is reevaluated for the "TEST" (bit 1, 2, 4) status, indicating the grinder operator has executed the second step of the test procedure to put probe housing 39 at roll surface 25.

At this time, a message "RUN TEST" is written in the status block area 230 on the CRT screen, and, the program jumps to read the NDT test defect signal amplitude, EA. If the MODE was set for RETEST, the program jumps to the Bar Plot (BRPL) subroutine and plots a vertical line for the NDT test defect signal amplitude, EA. If the MODE was set for 1st TEST, the program checks to determine if the NDT test defect signal, EA, is larger than any signal in array EC(0) already observed at the position-P. This provides for plot of only the largest or peak signal as the probe head is traversed across a defect region at position, P. The vertical bars plotted on the CRT display areas 235, 236 and 237 as positions P are in blue if the signal, EA, is less than the defect threshold, ECL, and, are plotted in red if they are larger than the defect amplitude threshold, ECL. At the end of the BRPL program the new signal EA is entered into the NDT test defect signal array (EC(P).

Following the bar plot, the subroutine returns to the main program to set the PC1 flat and place new position and defect data at the FIFO register 207 output by executing a Parallel Dump (PD) signal. The program then loops back to the beginning of Status Loop 2 to read Status Byte 2 (ST2). Following an affirmative FIFO register indication for FFR, the program continues in the second loop to read the position P, the NDT test defect signal, EA, and to plot the data at position P, on the CRT display.

If FFR indicates no data in the FIFO register 207, the program checks the STRT 2 status and loops to the beginning of Status Loop 2 to look again for new data or, if the ST2 byte indicates that the roll test is finished, the program will jump to the Status Loop 1 and execute the END OF TEST (E) subprogram, remaining in that loop until a new test is begun.

Figure 13:
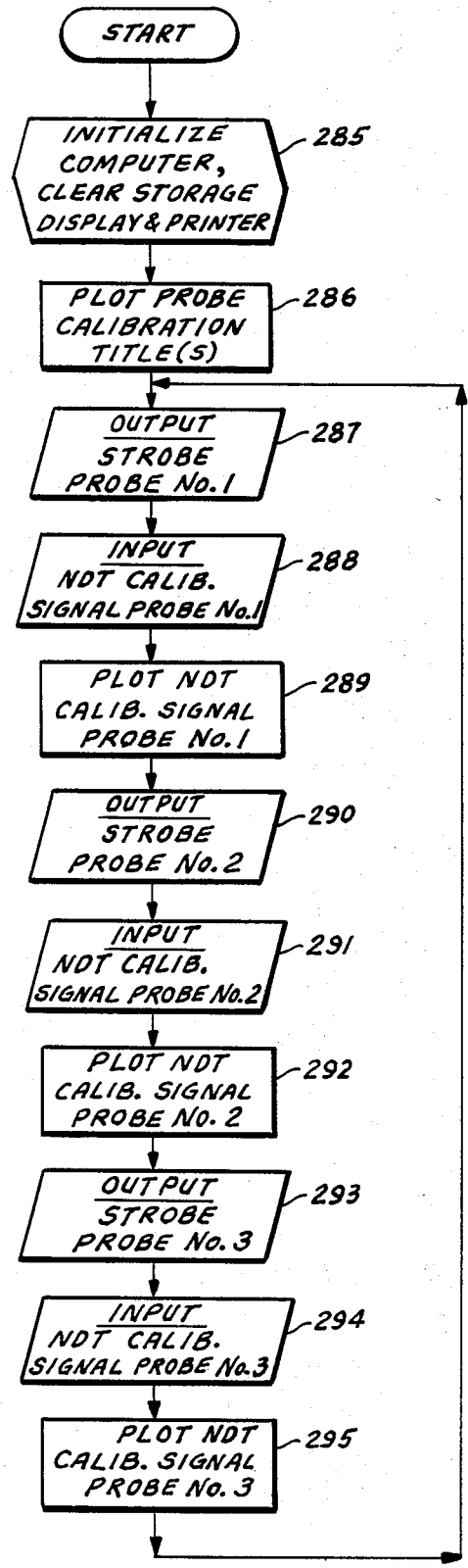
FIG. 13 is a flow chart of the computer software covering probe calibration in an off-line diagnostics subroutine.
Figure 15:
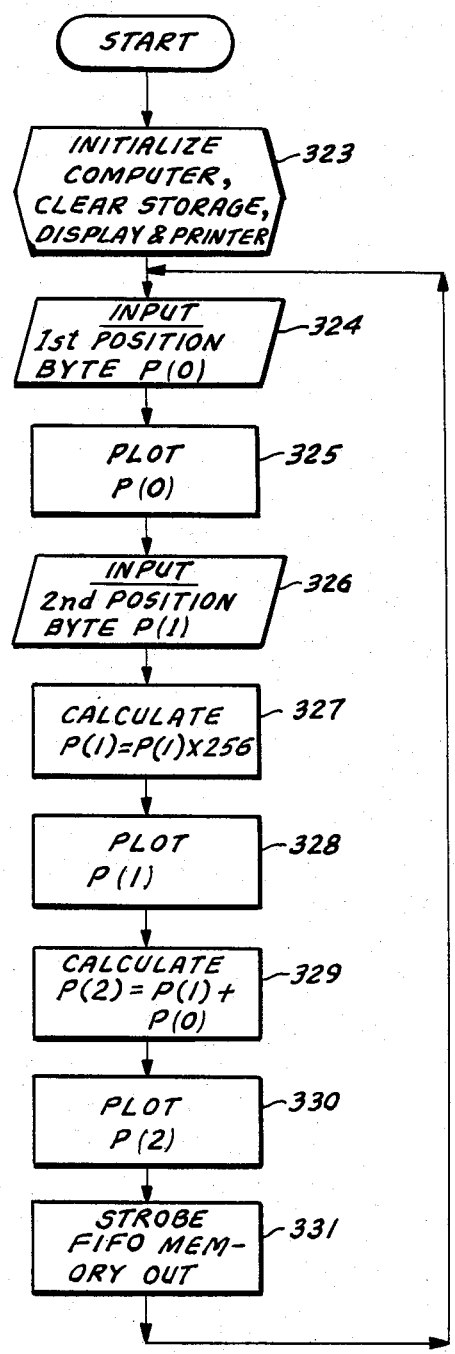
FIG. 15 is a flow chart of the computer software covering position sensor check in an off-line diagnostics subroutine.

FIGS. 13,14,15 are flow charts of OFF-LINE DIAGNOSTIC subroutines involving three equipment diagnostics subroutines which operate independently of each other, named PRBCAL probe calibration, STATST status signal test, and POSTST position sensor test, respectively. PRBCAL subroutine shown in FIG. 13 covers steps 285 to 295. STATST subroutine shown in FIG. 14 covers steps 296 to 322, and POSTST subroutine shown in FIG. 15 covers steps 323 to 331.

The PRBCAL program covered in steps 285 to 295, initializes the computer 160, line 219A,B outputs, the CRT terminal 176 and the CRT display 225 is formatted with PROBE CALIBRATIONS TESTS: 3=OK; 2=LO; 1=HI in display area 238 prior to simulating a defect. After a 5 second delay, Probe channel #1 is pulsed to obtain an artificial defect signal. The NDT test instrument 64 or 65 signal comparator 190 or 199 output (X) is read. If the value of X is:

3—Probe calibration is within a preset limit, for example, 3.3 volts $<X<4.3$ volts 2—Probe calibation is LOW; $X<3.3$ volts 1—Probe calibration is HIGH; $X>4.3$ volts The result of the test of probe channel #1 is written on the CRT screen in display are 238 in the following format "PROBE COMPARATOR 1=3" (or 2,1)

Signal comparators 191,192 in probe channels 2 and 3 are successively pulsed and the result written on the CRT screen in the same display area 238. The program loops to obtain a continuous series of tests for probe channels #1,#2 and #3.

The "STATST" program, covered in steps 296 to 322, itilializes the computer 160, the CRT terminal 176 for input of the STATUS BYTE with $A_o=A_1=0$. The status byte is read, and individual (6) bits are tested to determine and display in CRT display 225 at area 238 the Status Signals conditions:

BIT 1=1. "1ST TEST MORE" or "PLUG TEST MODE"

BIT 2=2. "PROBE ARM OUT" or "PROBE ARM NOT OUT"

Bit 3=3. "PROBE ARM DOWN" or "PROBE ARM NOT DOWN"

Bit 4=4. "FIFO (OR) READY" or "NO FIFO DATA"

Bit 5=5. "FIFO FULL" or "FIFO NOT FULL"

Bit 6=6. "78 INCH ROLL" or "54 INCH ROLL"

The program loops continuously and dynamic operation of the sensor read at the beginning will be indicated by the changes in the printed STATUS descriptors in CRT display area 238.

The POSTST program covered in steps 323 to 331, initializes the computer 160, CRT terminal 176 and readies the system for the position test. The $A_o$ and $A_1$ in the Output Byte are set to read the Position (low) Byte, P(0), and the Position (High) Byte P(1). Both bytes are printed in decimal numbers as well as the sum P(2) to obtain a printed line format on the CRT display 225 as follows:

P(0)=x x x x  P(1)=x x x x  P(2)=x x x x

The POSTST program is a continuous loop that prints another line on the CRT display 225 each time the program executes the loop. When the entire CRT screen is filled with 24 lines, the most recent date is entered at the bottom of the CRT display and the top line is "scrolled" out of the display. Changes in the position sensor are thus successively scrolled up the 24 lines of the CRT display each time the program loop executes.

We claim:

1. A computer-based nondestructive testing system for automatically inspecting roll surface conditions of a rolling mill roll rotatable in a test fixture and operable with a carriage movable substantially parallel and lengthwise of the test roll longitudinal axis, said system comprising:
   (a) nondestructive test probe means mounted on the movable carriage for generating at least one roll surface anomoly test signal;
   (b) means for automatically spacing the test probe means (a) from the roll surface by a gap having a fluid therein;
   (c) carriage movement sensor means on the carriage for generating a test probe means position signal relative to the distance along the roll length the test probe means has been carried by the movable carriage;
   (d) roll rotation sensor means in the rotatable test fixture for generating a roll circumference signal;
   (e) nondestructive test instrument means for processing at least one roll surface anomaly test signal from test probe means to produce an amplitude-variable roll surface defect signal; and
   (f) computer means for processing the amplitude-variable roll surface defect signal of (e), the test probe means position signal of (c) and the roll circumference signal of (d) comprising:
      (i) means for (1) converting the amplitude-variable roll surface defect signal into digital form, (2) detecting a digital defect signal peak and (3) allocating the digital defect signal peak into one of several preset levels in a memory device;
      (ii) means for (1) converting the test probe means position signal into digital form and (2) storing the digital position signal in the memory device of (f)(i)(3);
      (iii) means for (1) converting the roll circumference signal into digital form, and (2) storing the digital roll circumference signal in the memory device of (f)(i)(3); and
      (iv) means for coordinating the defect signal, test probe position signal and roll circumference signal for each inch of length of test roll surface scanned.

2. The apparatus of claim 1 wherein means (a) includes a test probe housing with a universal mount having at least one axis of movement between said housing and a support member.

3. The apparatus of claim 1 wherein said means (a) includes an articulated support arm mechanism having a test probe housing and means for automatically positioning said probe housing over and away from the test roll surface.

4. The apparatus of claim 1 wherein means (a) includes a test probe housing having at least one eddy current probe sensor to generate the anomoly test signal, and means (e) is an eddy current test instrument capable of processing each anomoly test signal.

5. The apparatus of claim 1 wherein means (a) includes a test probe housing having an ultrasonic probe sensor to generate the anomoly test signal, and means (e) is an ultrasonic test instrument capable of processing the anomoly test signal.

6. The apparatus of claim 1 wherein means (f) includes a roll defect plotting program for plotting bar signals representing the defect severity, and a display terminal for imaging the bar signals.

* * * * *